(12) United States Patent
De La Torre et al.

(10) Patent No.: US 11,195,103 B2
(45) Date of Patent: Dec. 7, 2021

(54) SYSTEM AND METHOD TO AID DIAGNOSIS OF A PATIENT

(71) Applicant: FUJITSU LIMITED, Kawasaki (JP)

(72) Inventors: Victor De La Torre, Madrid (ES); Boris Villazón-Terrazas, Madrid (ES)

(73) Assignee: FUJITSU LIMITED, Kawasaki (JP)

( * ) Notice: Subject to any disclaimer, the term of this patent is extended or adjusted under 35 U.S.C. 154(b) by 502 days.

(21) Appl. No.: 15/416,630

(22) Filed: Jan. 26, 2017

(65) Prior Publication Data
US 2017/0277840 A1    Sep. 28, 2017

(30) Foreign Application Priority Data

Mar. 24, 2016  (DE) ...................... 10 2016 205 064.8
Mar. 24, 2016  (GB) ...................................... 1605112

(51) Int. Cl.
| | |
|---|---|
| *G06N 5/02* | (2006.01) |
| *G16H 50/20* | (2018.01) |
| *G06N 20/20* | (2019.01) |
| *A61B 5/00* | (2006.01) |

(52) U.S. Cl.
CPC ........... *G06N 5/022* (2013.01); *A61B 5/7271* (2013.01); *G06N 20/20* (2019.01); *G16H 50/20* (2018.01)

(58) Field of Classification Search
None
See application file for complete search history.

(56) References Cited

U.S. PATENT DOCUMENTS

| | | |
|---|---|---|
| 8,731,968 B1 | 5/2014 | Iliff |
| 2002/0091687 A1* | 7/2002 | Eglington .............. G16H 50/20 |
| 2008/0048367 A1 | 2/2008 | Falat |
| | (Continued) | |

FOREIGN PATENT DOCUMENTS

| | | |
|---|---|---|
| CN | 201312798 Y | 9/2009 |
| JP | 2009-110490 | 5/2009 |
| KR | 10-2012-0087492 | 8/2012 |

OTHER PUBLICATIONS

Juan F. Cia, Neo4j: What a graph database is and what it is used for, May 22, 2015, BBVA (Year: 2015).*

(Continued)

*Primary Examiner* — Aryan E Weisenfeld
*Assistant Examiner* — Karen A Hranek
(74) *Attorney, Agent, or Firm* — Staas & Halsey, LLP

(57) ABSTRACT

A system and method to input patient data including previous diagnosis, drugs, symptoms and treatment, open data and expert knowledge, and to use these inputs to create a patient clinical object (PCO), biomedical knowledge and rule based knowledge graphs, and to enrich the PCO using the biomedical knowledge graph. A meta diagnosis predictor is to use the PCO and the biomedical knowledge graph and/or the rule based knowledge graph in plural predictors of a diagnosis-based predictor to provide a set of diagnoses based on previous diagnoses, a drug-based predictor to provide a set of diagnoses based on drugs taken by the patient, a symptom-based predictor to provide a set of diagnoses based on symptoms of the patient and a treatment-based predictor to provide a set of diagnoses based on the treatments. Any of the sets of diagnoses may be combined to give a predicted primary diagnosis for the patient.

5 Claims, 10 Drawing Sheets

(56) References Cited

U.S. PATENT DOCUMENTS

| | | | |
|---|---|---|---|
| 2010/0318381 A1* | 12/2010 | Iliff | G06Q 50/22 705/3 |
| 2011/0060604 A1 | 3/2011 | Bangara et al. | |
| 2011/0119212 A1* | 5/2011 | De Bruin | A61B 5/00 706/12 |
| 2011/0225114 A1* | 9/2011 | Gotthardt | G06F 21/6245 706/50 |
| 2012/0130743 A1 | 5/2012 | Gotthardt et al. | |
| 2013/0226618 A1* | 8/2013 | Eisenhandler | G06Q 50/24 705/3 |
| 2013/0282396 A1* | 10/2013 | Lagor | G16H 50/70 705/2 |
| 2015/0363553 A1 | 12/2015 | Rustgi et al. | |
| 2016/0012341 A1 | 1/2016 | Raman | |

OTHER PUBLICATIONS

UKIPO Search Report dated Aug. 30, 2016 in corresponding Great Britain Patent Application No. GB1605112.0 (5 pages).

"A method for inferring medical diagnoses from patient similarities"; Assaf Gottlieb et al.; PMCID: PMC3844462; BMC Med. 2013; 11: 194; published online Sep. 2, 2013. ; (11 pages).

"Diagnostic Prediction for Social Anxiety Disorder via Multivariate Pattern Analysis of the Regional Homogeneity"; Wenjing Zhang et al.; BioMed Research International vol. 2015 (2015), Article ID 763965, 9 pages; (7 pages).

"Prediction and early diagnosis of complex diseases by edge-network"; Xiangtian Yu et al.; Bioinformatics Advance Access published Oct. 31, 2013; (9 pages).

German Search Report dated Sep. 5, 2016 in corresponding German Patent Application No. 102016205064.8 (9 pages).

Extended European Search Report dated Mar. 17, 2017 in related European Patent Application No. 16201277.7 (11 pages).

\* cited by examiner

SYSTEM AND METHOD TO AID DIAGNOSIS OF A PATIENT

CROSS-REFERENCE TO RELATED APPLICATIONS

This application claims the benefits of United Kingdom Application No. 1605112.0, filed Mar. 24, 2016, in the United Kingdom Intellectual Property Office, and German Application No. 102016205064.8 filed Mar. 24, 2016 in the German Intellectual Property Office, the disclosures of which are incorporated herein by reference.

BACKGROUND

1. Field

The present invention relates to diagnosis of an individual or subject, usually referred to as a patient. The patient may be a human or potentially an animal, such as a specimen of a rare breed or even a pet. In many scenarios, the patient may already be suffering from a disorder, but in others the patient is currently healthy. The invention is thus widely applicable in medicine, healthcare and veterinary science.

2. Description of the Related Art

The diagnosis process is an estimation of the probability that a specific outcome or disease (or condition, usually including illness or disorder) is present (or absent) within an individual.

Providing an accurate diagnosis for a patient is a challenging task. Years of study and daily practice provide clinicians (for example these could include nurses, doctors, dentists, healthcare practitioners and veterinary practitioners) with the skills necessary to estimate this diagnosis. The accuracy of this estimation is crucial to provide the patient with the right treatment. However due to the complexity of the task, a high level of accuracy is not always achieved. An error at the diagnosis level has a deep impact on patient health, since almost all treatments have secondary effects. In the case of mental health, for example, estimating the right diagnosis could be even a more difficult task given the complexity of human behaviour.

Nowadays, diagnostic errors (which can be defined as a diagnosis that is missed, wrong or delayed, as detected by some subsequent definitive test or finding) are clinically and financially more costly than even before. Moreover, diagnostic errors are the leading cause of medical malpractice claims in the U.S. and are estimated to cause 40000-80000 deaths annually.

There are several factors that affect the accuracy of the diagnosis estimation:
- Clinicians have a very short time to see the patient
- Diagnoses are not obvious in many cases, since several symptoms might be simultaneously present
- The "resolution" of the diagnosis has to meet the existent treatments
- A given patient is diagnosed by different class of clinicians, from several specialities and different levels of knowledge
- Previous diagnoses recorded in the databases might not reflect the real condition of the patient due to errors when such previous diagnoses are recorded in the information system.

Consequently, assisting clinicians during the diagnosis process will reduce the diagnosis errors and therefore will improve the efficiency of the healthcare system and also reduce costs by avoiding undesirable secondary effects.

SUMMARY

An embodiment according to a first aspect of the invention provides a system to aid diagnosis of a patient, comprising: a data and knowledge acquisition module and a meta diagnosis prediction module, wherein: the data and knowledge acquisition module includes: an input for patient data including any of previous diagnosis, drugs, symptoms and treatment, an input for open data and an input for expert clinician knowledge, and is arranged to use these inputs to create a patient clinical object, PCO, a biomedical knowledge graph and a rule based knowledge graph, and then to enrich the patient clinical object using the biomedical knowledge graph; the meta diagnosis prediction module is arranged to use the patient clinical object and the biomedical knowledge graph and/or the rule based knowledge graph in two or more of the following predictors: a diagnosis-based predictor to provide a set of diagnoses based on previous diagnoses, a drug-based predictor to provide a set of diagnoses based on drugs taken by the patient, a symptom-based predictor to provide a set of diagnoses based on symptoms of the patient and a treatment-based predictor to provide a set of diagnoses based on the treatments the patient is receiving; and wherein the meta diagnosis prediction module includes a meta predictor to combine the sets of diagnoses to give a predicted primary diagnosis.

This mixture of patient-specific data, open data and clinician's knowledge and its processing according to invention embodiments gives valuable results in terms of a predicted primary diagnosis. The predicted primary diagnosis may be displayed to a clinician on screen, or provided in any other suitable way, for example as a print out or email.

In preferred embodiments, all of the individual predictors are used, to give a full range of predictions based on all the different factors that can be considered. Each predictor takes patient-specific information from the PCO and general information from at least one of the expert knowledge base and biomedical knowledge base. In one embodiment, the meta diagnosis prediction module makes predictions by organizing and processing the predictions produced by the individual predictors, i.e., diagnosis based, drug-based, symptom-based, or treatment-based.

The diagnosis-based predictor can be arranged to provide a set of diagnoses based on a previous diagnosis, for example using a previous diagnosis (or previous diagnoses) in the PCO with input from the rule-based graph to add expert knowledge.

The drug-based predictor can be arranged to provide a set of diagnoses based on drugs taken by the patient using information from the PCO and the biomedical knowledge graph.

The symptom-based predictor can be arranged to provide a set of diagnoses based on symptoms of the patient using information in the PCO and the biomedical knowledge graph.

Finally, the treatment-based predictor can be arranged to provide a set of diagnoses based on the treatments in the PCO and the biomedical knowledge graph.

Preferably, the input for expert clinician knowledge allows input of pairs of two (or groups of three or more) diagnoses and a relation between them that is known to the clinician. For example input this can be in the form of a plain text file. The data and knowledge acquisition module can include an expert knowledge base engine to build a graph from these diagnoses and the relations between them.

The data and knowledge acquisition module may be arranged to extract data from the open sources to form the biomedical knowledge graph, for example as a graph database that contains information about diagnoses, drugs, treatments and symptoms and the links between them.

The data and knowledge acquisition module can include a PCO engine, providing the PCO from historical clinical data as a graph centred on the patient, with information about the patient linked to the patient by categories, such as any of diagnosis, symptom, treatment, hospital visit and prescription. The historical clinical data may be provided, for example from hospital records, or health authority records.

A PCO enricher may provided in the data and knowledge acquisition system, to compare the PCO with the biomedical knowledge graph to equate PCO parts with standard vocabulary and to annotate entities in the PCO with corresponding concepts/information from the biomedical knowledge graph.

The meta diagnosis prediction module can work in any suitable fashion to arrive at an overall primary diagnosis taking into account the various individual predictors used. For example, it may ranks each diagnosis in each set of diagnoses (from an individual predictor) based on a score. As an aside, a set of diagnoses might in fact contain a single diagnosis.

Also, each predictor may be given a weighting based on an accuracy of performance measure. This weighting can be used to determine the number of diagnoses (starting from the top-ranking diagnosis and working downwards in each set of diagnoses) taken into consideration for the primary diagnosis. In this arrangement some of the set of diagnoses are not taken into consideration.

The accuracy of performance measure can be derived any suitable way. In one example it is derived from meta predictor training on a pre-defined set of training examples.

The meta predictor can check the diagnoses taken into consideration from the predictors and select one or more. For example it can select the diagnosis which is present in the highest number of predictors or has the highest cumulative score as the primary diagnosis.

According to an embodiment of a further aspect of the invention there is provided a method to aid diagnosis of a patient, comprising: accepting input of patient data including any of previous diagnosis, drugs, symptoms and treatment, accepting input of open data and accepting input of expert clinician knowledge, and using these inputs to create a patient clinical object, PCO, a biomedical knowledge graph and a rule based knowledge graph, and then enriching the patient clinical object using the biomedical knowledge graph; using the patient clinical object and the biomedical knowledge graph and/or the rule based knowledge graph to provide two or more of the following predictions: a diagnosis-predicted set of diagnoses based on previous diagnoses, a drug-based predicted set of diagnoses based on drugs taken by the patient, a symptom-based predicted set of diagnoses based on symptoms of the patient and a treatment-based predicted set of diagnoses based on the treatments the patient is receiving; and combining the sets of diagnoses to give a predicted primary diagnosis.

According to an embodiment of a further aspect of the invention there is provided a computer program which when executed on a computer carries out a method to aid diagnosis of a patient, comprising: accepting input of patient data including any of previous diagnosis, drugs, symptoms and treatment, accepting input of open data and accepting input of expert clinician knowledge, and using these inputs to create a patient clinical object, PCO, a biomedical knowledge graph and a rule based knowledge graph, and then enriching the patient clinical object using the biomedical knowledge graph; using the patient clinical object and the biomedical knowledge graph and/or the rule based knowledge graph to provide two or more of the following predictions: a diagnosis-predicted set of diagnoses based on previous diagnoses, a drug-based predicted set of diagnoses based on drugs taken by the patient, a symptom-based predicted set of diagnoses based on symptoms of the patient and a treatment-based predicted set of diagnoses based on the treatments the patient is receiving; and combining the sets of diagnoses to give a predicted primary diagnosis.

A method or computer program according to preferred embodiments of the present invention can comprise any combination of the previous apparatus aspects, without restriction as to the specific parts of the system involved. Methods or computer programs according to these further embodiments can be described as computer-implemented in that they require processing and memory capability.

The apparatus according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer configures the computer to become the system according to any of the preceding system definitions or any combination thereof.

According to a further aspect there is provided a program which when loaded onto the at least one computer configures the at least one computer to carry out the method steps according to any of the preceding method definitions or any combination thereof.

In general the computer may comprise the elements listed as being configured or arranged to provide the functions defined. For example this computer may include memory, processing, and a network interface.

The invention can be implemented in digital electronic circuitry, or in computer hardware, firmware, software, or in combinations of them. The invention can be implemented as a computer program or computer program product, i.e., a computer program tangibly embodied in a non-transitory information carrier, e.g., in a machine-readable storage device, or in a propagated signal, for execution by, or to control the operation of, one or more hardware modules. A computer program can be in the form of a stand-alone program, a computer program portion or more than one computer program and can be written in any form of programming language, including compiled or interpreted languages, and it can be deployed in any form, including as a stand-alone program or as a module, component, subroutine, or other unit suitable for use in a data processing environment. A computer program can be deployed to be executed on one module or on multiple modules at one site or distributed across multiple sites and interconnected by a communication network.

Method steps of the invention can be performed by one or more programmable processors executing a computer program to perform functions of the invention by operating on input data and generating output. Apparatus of the invention can be implemented as programmed hardware or as special purpose logic circuitry, including e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions coupled to one or more memory devices for storing instructions and data.

The invention is described in terms of particular embodiments. Other embodiments are within the scope of the following claims. For example, the steps of the invention can be performed in a different order and still achieve desirable results. Multiple test script versions can be edited and invoked as a unit without using object-oriented programming technology; for example, the elements of a script object can be organized in a structured database or a file system, and the operations described as being performed by the script object can be performed by a test control program.

Elements of the invention have been described using the terms "module" and "unit" and functional definitions. The skilled person will appreciate that such terms and their equivalents may refer to parts of the system that are spatially separate but combine to serve the function defined. Equally, the same physical parts of the system may provide two or more of the functions defined.

For example, separately defined means may be implemented using the same memory and/or processor and/or input/output as appropriate.

BRIEF DESCRIPTION OF THE DRAWINGS

Preferred features of the present invention will now be described, purely by way of example, with references to the accompanying drawings, in which.

DETAILED DESCRIPTION

Figure 1:
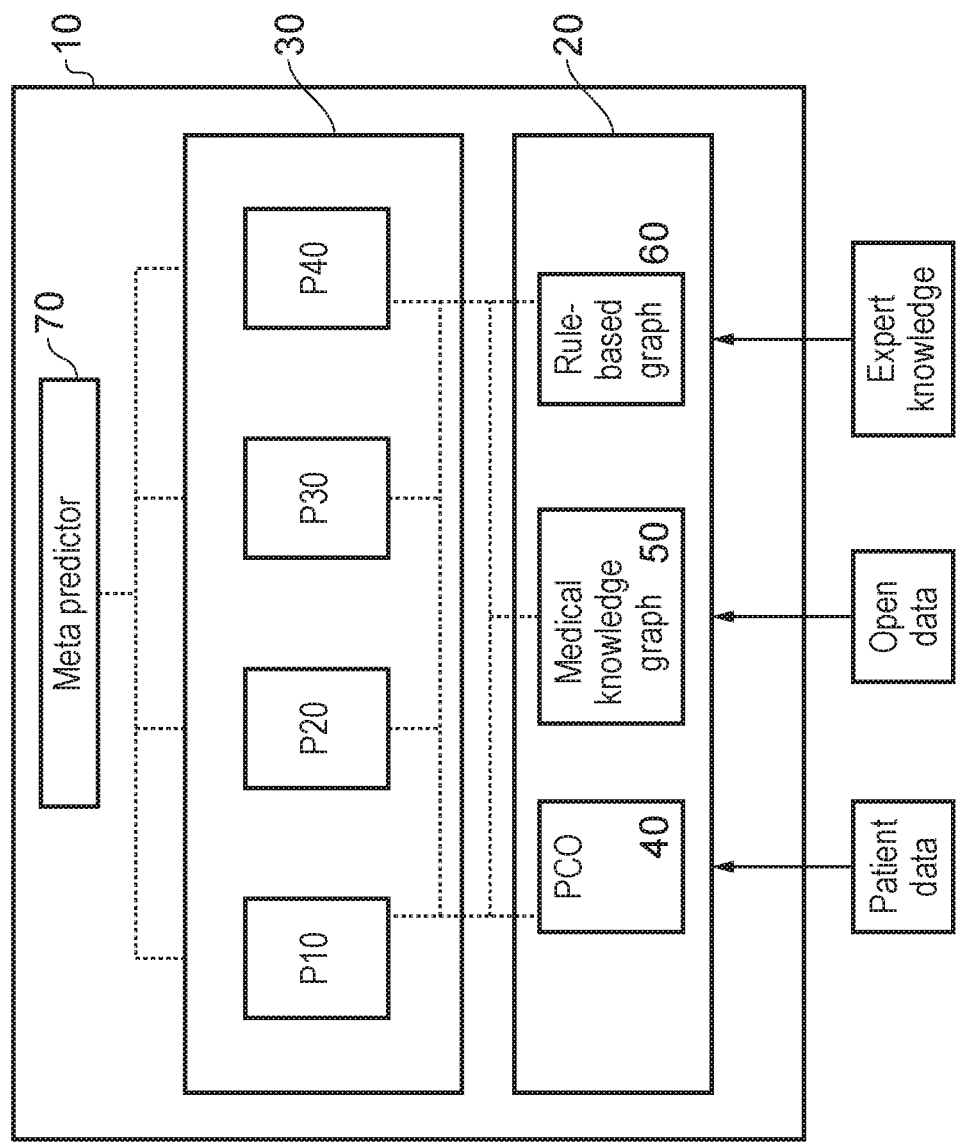
FIG. 1 is a block diagram of components in a general embodiment of the invention.
Figure 2:
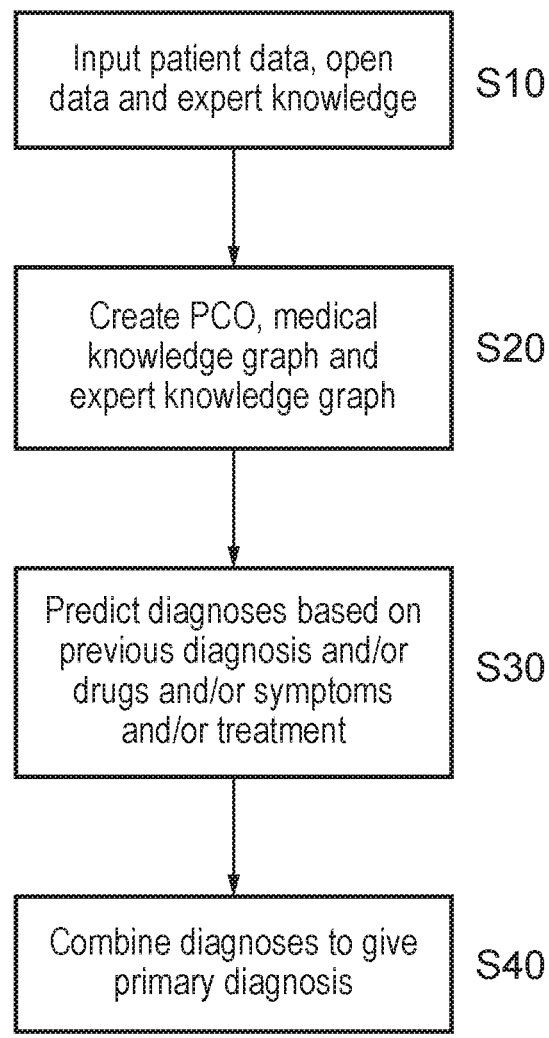
FIG. 2 is a flow chart of a method in a general embodiment.

Getting the right diagnosis is a key aspect of healthcare, as it provides an explanation of the patient's health problem and informs subsequent health care decisions Diagnostic errors can lead to negative health outcomes, psychological distress, and financial costs. If a diagnostic error occurs, inappropriate or unnecessary treatment may be given to a patient, or appropriate, and potentially lifesaving, treatment may be withheld or delayed. However, efforts to identify and mitigate diagnostic errors have so far been quite limited. Prior art methods using data to aid diagnosis may, for example, exploit similarities between patients along multiple dimensions to predict the eventual discharge diagnosis, exploit family links or rely on tests or medical hardware.

However, prior art systems do not take into account multiple factors such as patient clinical history, previous diagnoses, biomedical research literature, drugs prescription and dispensation, and existing medical knowledge (for example in the area of mental health).

The inventors have come to the realisation that it would be desirable to provide:
methods that generate patient related information annotated with medical concepts, such as diagnoses, symptoms, treatments, diseases/conditions, drugs extracted from health standards, and biomedical research literature;
methods that combine the aforementioned knowledge base with domain expert knowledge in order to have a complete snapshot of patients;
methods that mine that big knowledge base in order to get as many relevant features as possible, for example for mental health diagnosis, and combine them to support the diagnosis and reduce diagnostic errors.

The goal of invention embodiments is to reduce the medical diagnosis error, for example in the psychiatric area. The system extracts knowledge from heterogeneous data sources such as the patient's clinical data, bio-medical ontologies, and medical guidelines and uses this information to estimate the current diagnosis of a patient. The diagnosis predicted together with supplementary information supporting the result is then available to the clinician who makes the final decision.

Embodiments of the invention may:
create a biomedical knowledge base for representing health related concepts, for example mental health related concepts, which can be extracted from the literature via public data sources together with the clinicians' expertise on diagnoses;
create a "Patient Clinical Object", which is a term coined as a semantically rich aggregation of clinical entities that encapsulates information about a given patient, such as clinical history, diagnoses, drugs, treatments (non-drug treatments such as surgical produces, therapies);
develop a diagnosis mechanism that include as many relevant features as possible for the diagnosis, and which takes as input the biomedical knowledge base and the Patient Clinical Object (PCO).

Precision medicine is a medical model that proposes the customisation of healthcare, tailored to the individual patient/subject. This is an emerging approach for disease/condition diagnosis, treatment and prevention that takes into account individual variability in genes, physiology, anatomy, environment, and lifestyle. In this context, invention embodiments support the individual variability of the patients by reducing medical diagnosis errors. Invention embodiments will help providers, payers, and consumers to sift through the volumes of medical information and recommendations to aid with medical diagnosis and treatment.

The following definitions are used in this document:

Diagnosis: the process of determining by examination the nature and/or circumstance of a disease or condition from its signs and symptoms.

Medical diagnosis error: a diagnosis that is missed, wrong or delayed, as detected by some subsequent definitive test or finding.

Medical treatment: the management and care of a patient, including for example in the mental health area, nursing, psychological intervention and specialist mental health rehabilitation. This term may also include "alternative" medical treatments and medication which may be prescribed, if so wished, for example, homeopathic/hypnosis/acupuncture treatment.

Drugs: medications that treat or prevents or alleviates the symptoms of a disease or condition.

FIG. 1 shows a general embodiment of the invention. A system 10 is designed to aid diagnosis of a patient (and in fact can provide a diagnosis alone from patient data, open data and general expert knowledge, without a clinician's additional input). The system includes a data and knowledge acquisition module 20 which takes in and works on this data to produce useful outputs, for example in the form of the PCO 40, biomedical expert knowledge graph 50 and rule-based knowledge graph 60. There is also a meta diagnosis prediction module 30 which used these products to provide predictions using predictors P10 to P40. Each predictor provides a prediction based on a different factor or viewpoint. These predictions are combined to give a final prediction.

Looking at the modules in more detail, the data and knowledge acquisition module includes: an input for patient data including, for example, previous diagnosis, drugs, symptoms and treatment, an input for open data and an input for expert clinician knowledge. It is arranged to use these inputs to create the PCO, biomedical knowledge graph and rule based knowledge graph, and then to enrich the patient clinical object using the biomedical knowledge graph. Here, enriching includes comparison of the PCO with the biomedical knowledge graph to equate PCO parts with standard vocabulary and hence to annotate entities in the patient data as necessary with corresponding concepts/information from the biomedical knowledge graph. This facilitates later use of the PCO in conjunction with the other standard data.

The meta diagnosis prediction module can use the patient clinical object, the biomedical knowledge graph and the rule based knowledge graph in predictors. For example a diagnosis-based predictor can provide a diagnosis based on previous diagnoses using previous diagnoses with input from the rule-based graph 60 to add expert knowledge. A drug-based predictor can provide a diagnosis based on drugs taken by the patient using the PCO and biomedical knowledge graph. A symptom-based predictor can provide a diagnosis based on symptoms of the patient using the PCO and biomedical knowledge graph. Finally, a treatment-based predictor can provide a diagnosis based on the treatments the patient is receiving (from the PCO) and add knowledge from the biomedical knowledge graph. All three data sets (the PCO, which may be in graph form and the biomedical and rule-based graphs) can be also be used in combination where appropriate.

The meta diagnosis prediction module includes a meta predictor to combine the diagnoses in any suitable way to give an overall predicted diagnosis.

Some key features of some invention embodiments are:
  The inclusion of as many relevant features as possible for the diagnosis, reducing health diagnostic errors.
  The selection of the data sources, the process of generating the internal datasets, the relevant features selection and validation can be examined closely by the experts by means of a knowledge acquisition module.
  The use of "Patient Clinical Objects" (PCO). This term is coined as a semantically rich aggregation of clinical entities (information objects) that encapsulates information about a given patient. The PCO contains information about the patient and their clinical data, diagnoses, treatments, symptoms and drugs. This information is linked to the healthcare resources/entities. Moreover, the PCO will evolve by including more medical information about the patient over time.

The solution in invention embodiments can rely on a set of relevant features that affect the (mental) health diagnosis. The system to carry this out can consist of two main modules:
  A module that collects, extracts and integrates healthcare data including domain expert knowledge, patient clinical data, and open data, to create a knowledge base.
  A module that mines the knowledge base, identifies all the relevant features for (e.g. mental) health diagnoses, and combines/aggregates them to support the diagnosis and reduce diagnostic errors.

Figure 3:
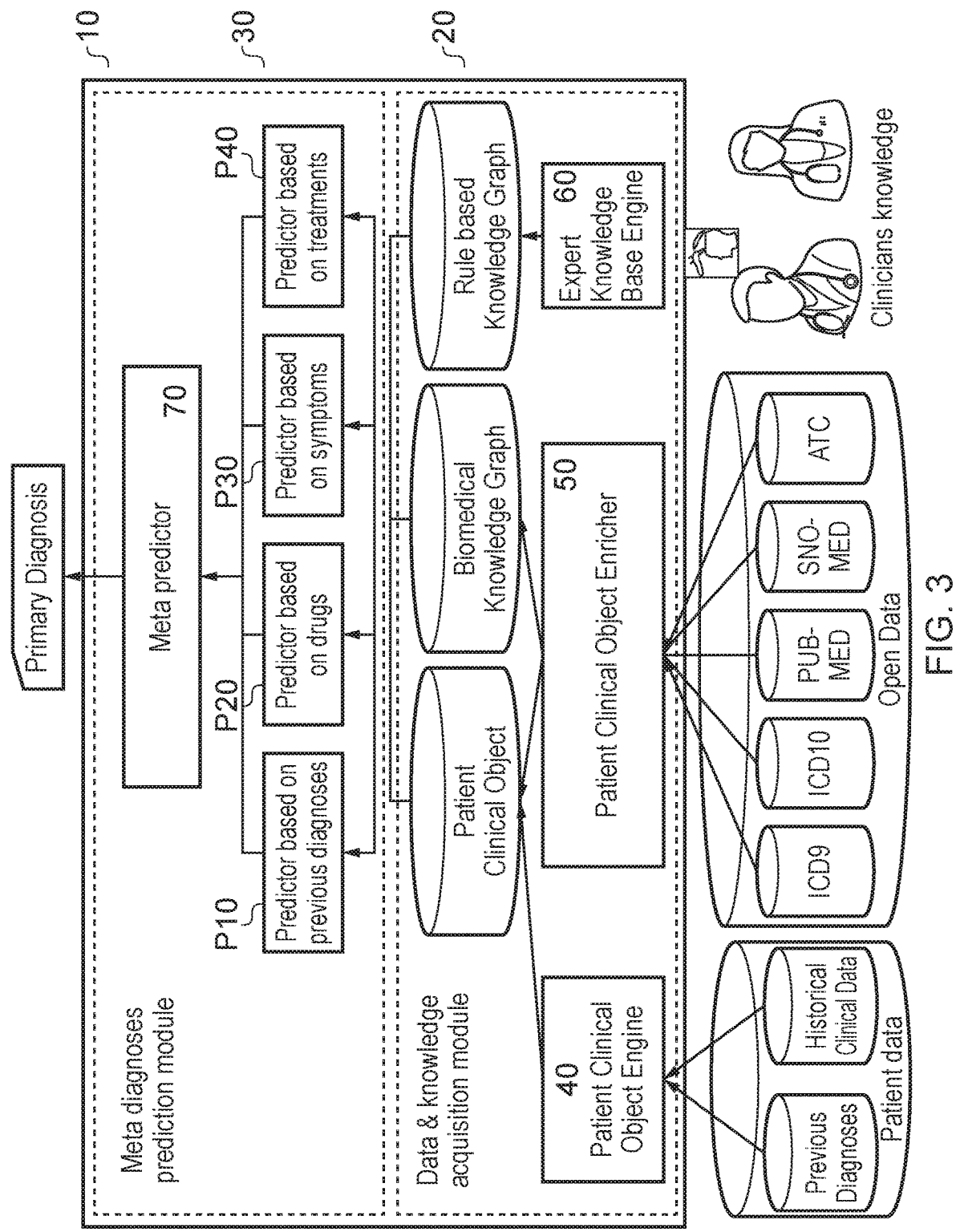
FIG. 3 is a block diagram of the main system components in a detailed embodiment.

The system includes a data and knowledge acquisition module and a meta diagnosis prediction module. FIG. 3 shows the main components of the proposed solution.

Data and Knowledge Acquisition Module 20

This module takes as input the following information:
  Expert knowledge provided by doctor/clinicians in the form of rules. The clinicians input the rules as text plain files. Basically, the file consists of several rows, and each row contains 2 diagnoses and the relation between them. For example:
    Diagnosis1, relationA, Diagnosis2
    Diagnosis3, relationB, Diagnosis4
  Examples of rules are incompatible diagnoses, and prevalence of diagnosis
    290.0, prevailing over, 290.4
    300.0, incompatible with, 309
  Where 290.0 corresponds to Senile dementia, uncomplicated, and 290.4 corresponds to Vascular dementia. Also, 300.0 corresponds to Anxiety states, and 309 corresponds to Adjustment reaction.
  Previous diagnoses provided by other clinicians as they are recorded in the patient clinical history. These diagnoses will be based on existing international standards such as ICD9 and ICD10 (The ninth and tenth revisions of the International Classification of Diseases).
  Data related to the patient's visits to the hospital and the associated points of care, including the frequency, timeframe, and what resources the patient has used.
  Biomedical research literature, extracted e.g. from PUBMED, related to diagnoses, diseases/conditions, treatments, etc. PUBMED is a service of the US National Library of Medicine (NLM) and provides free access to the NLM database of nursing, veterinary, healthcare, medical and scientific articles.
  Prescription and dispensation of drugs, and their adverse drug reaction, based on European and international standards, such as ATC.
  A set of knowledge extracted from available medical standards such as SNOMED. SNOMED CT (clinical terms) is a standardised multilingual vocabulary which is generally applicable across medical and health care areas.

This module collects, extracts, integrates, curates and cleans the aforementioned data sources and produces the following datasets:
  1. Patient Clinical Object, which contains all the related information about the patient, namely age group, gender, a list of hospital visits grouped by unit, e.g., emergency room, outpatient, inpatient, and day hospital, and a list of previous diagnoses grouped by hospital visits and units.
  2. Biomedical Knowledge Graph, which contains all the biomedical knowledge from the literature and available standards. This resource is used to annotate the patient data (previous diagnoses, historical clinical data) already curated and pre-processed in terms of treatments, diagnoses, drugs, and symptoms as explained in more detail later.
3. Rule based Knowledge Graph, which contains the knowledge from the clinicians and is later applied to the diagnosis support process.

Meta Diagnoses Prediction Module 30

The primary diagnosis prediction module is a meta-predictor, also known as hybrid/combined predictor that make predictions by organizing and processing the predictions produced by two or more predictors. The individual predictors take the information for the relevant features from the Patient Clinical Object, Biomedical Knowledge Graph and Rule based Knowledge Graph.

Individual predictors produce one or more potential diagnoses, scored according to known metrics for probability of facts taking into account two or more data sources, one of which is the PCO.

The individual predictors can be:
Predictor based on previous diagnoses. In this case the prediction is made by checking and reviewing the previous diagnoses of the patient, re-interpreting those diagnoses according to clinicians' rules, and categorizing the diagnosis in two main levels, in relation to the rules provided by the clinicians, for example Level 1 and Level 2.
Predictor based on the drugs the patient was taking. All the information related to drugs is extracted from the Patient Clinical Object, and the Biomedical Knowledge Graph.
Predictor based on the symptoms of the patient. The symptoms and their relation with the patient are extracted from Patient Clinical Object and Biomedical Knowledge Graph.
Predictor based on the treatments the patient is receiving. The treatments along patient data are extracted from Patient Clinical Object and Biomedical Knowledge Graph.

The meta predictor component combines results of the individual predictors in order to offer better predicting performance. To this end, the component adjusts weights to each one of the predictors. In the following equation $$D_j = W_d P_d + W_{dr} P_{dr} + W_s P_s + W_t P_t$$

Where
$D_j$ is the predicted diagnosis
$W_d$ is the assigned weight to the predictor based on previous diagnosis
$P_d$ is the prediction based on previous diagnosis
$W_{dr}$ is the assigned weight to the predictor based on drugs the patient was taking
$P_{dr}$ is the prediction based on drugs the patient was taking
$W_s$ is the assigned weight to the predictor based on symptoms of the patient
$P_s$ is the prediction based on symptoms of the patient.
$W_t$ is the assigned weight to the predictor based on treatments of the patient
$P_t$ is the prediction based on treatments of the patient The component takes a sample from the population of patients and creates a training dataset. The goal of the component is to build an algorithm that automatically applies the predictors, and makes a best guess or estimate the primary diagnosis.

Figure 4:
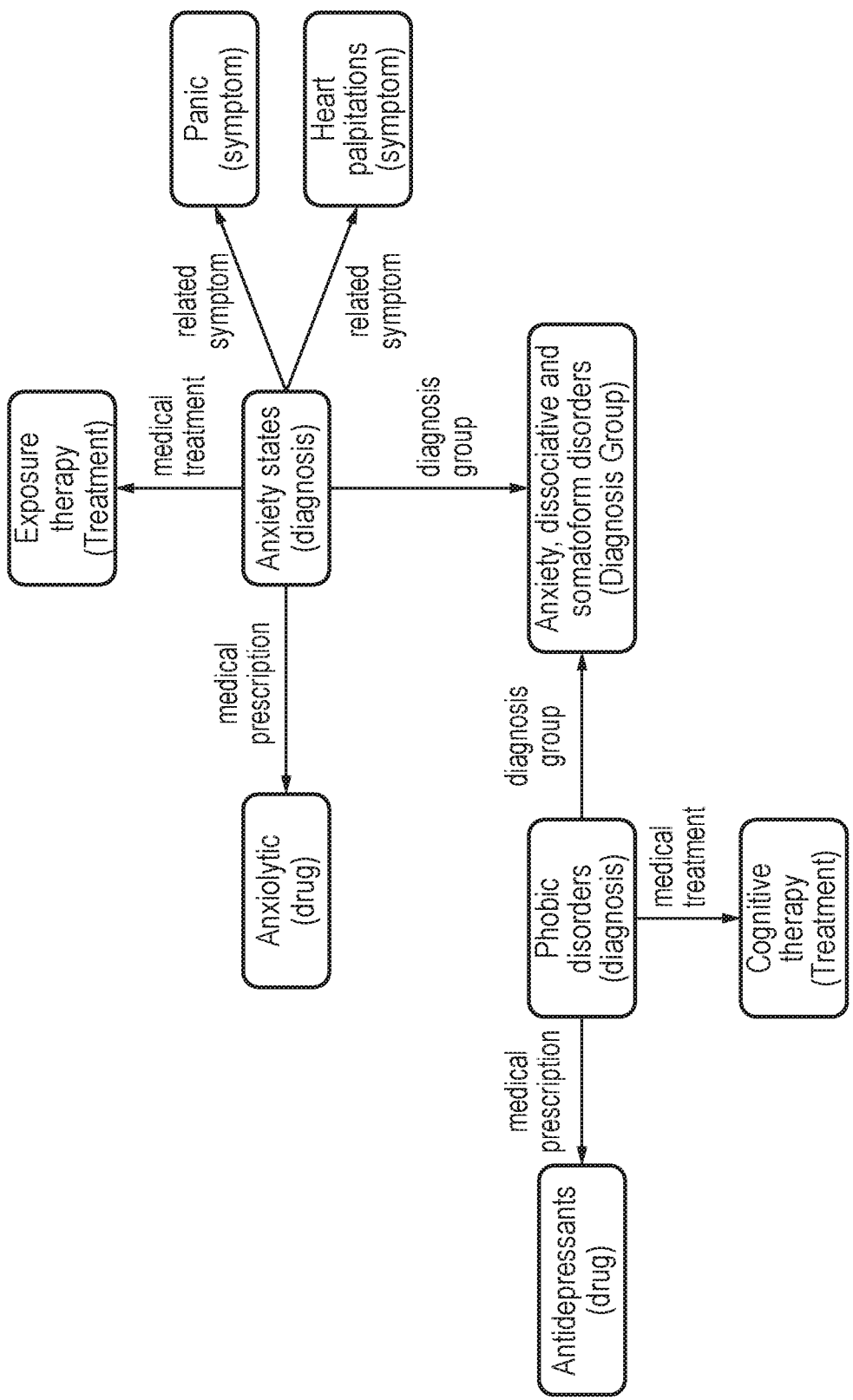
FIG. 4 is an excerpt from a biomedical knowledge graph.
Figure 5:
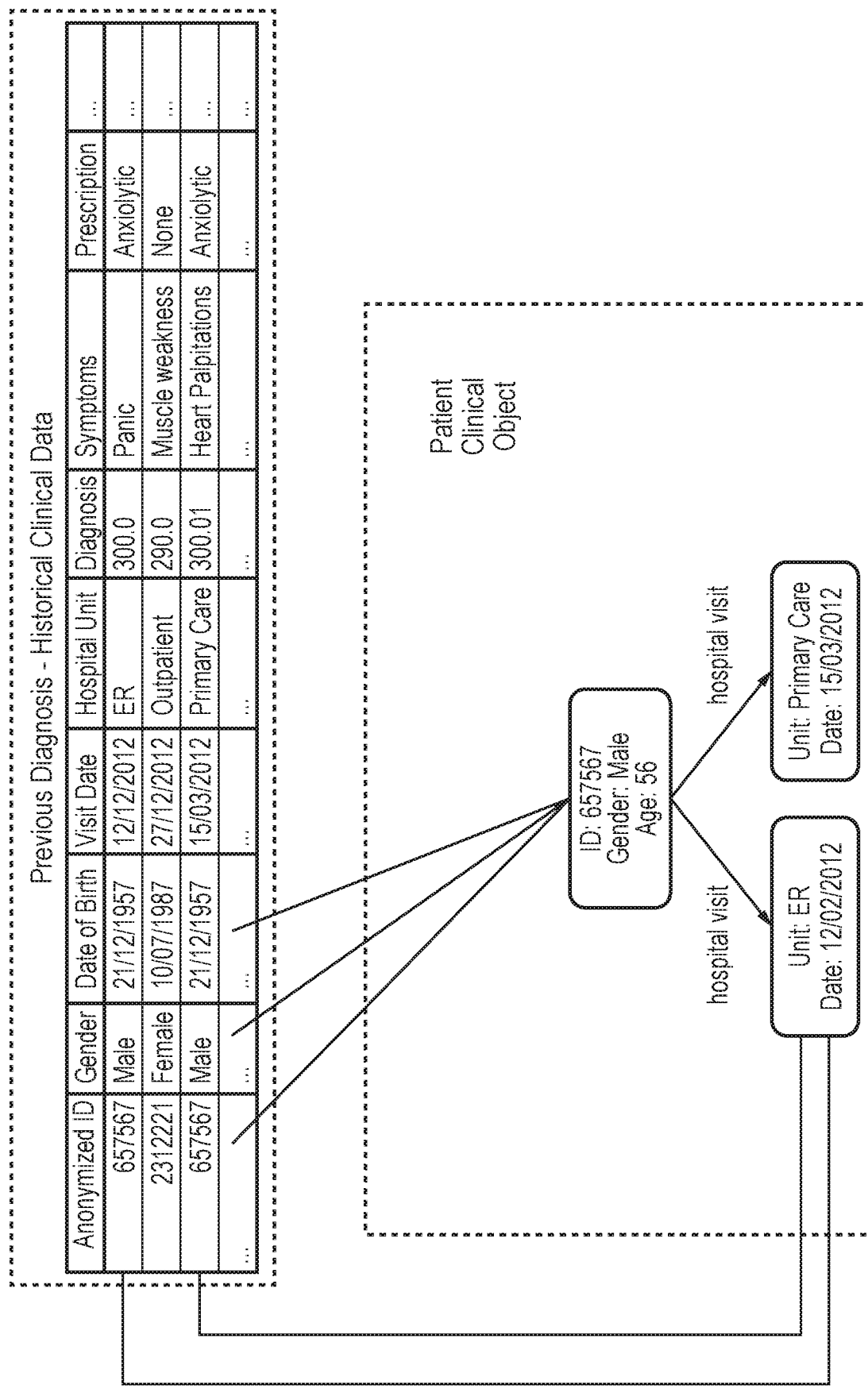
FIG. 5 is an example PCO.

FIGS. 4 to 7 illustrate a worked example. FIG. 5 shows a PCO in the form of a graph centered on the patient. This is an example with simple data.

The graph includes patient information such as gender, age, and anonymized ID. Moreover, it also contains information about what are the diagnoses of the patient, what are his/her symptoms, treatments and drugs. Finally, the graph includes the patient historical visits.

FIG. 4 is an example of the way that biomedical related information is encoded in a graph. This is the Biomedical Knowledge Graph, a graph database that contains information about diagnoses, drugs, treatments, and symptoms, and the relations between them. FIG. 4 shows an excerpt only.

Figure 6A:
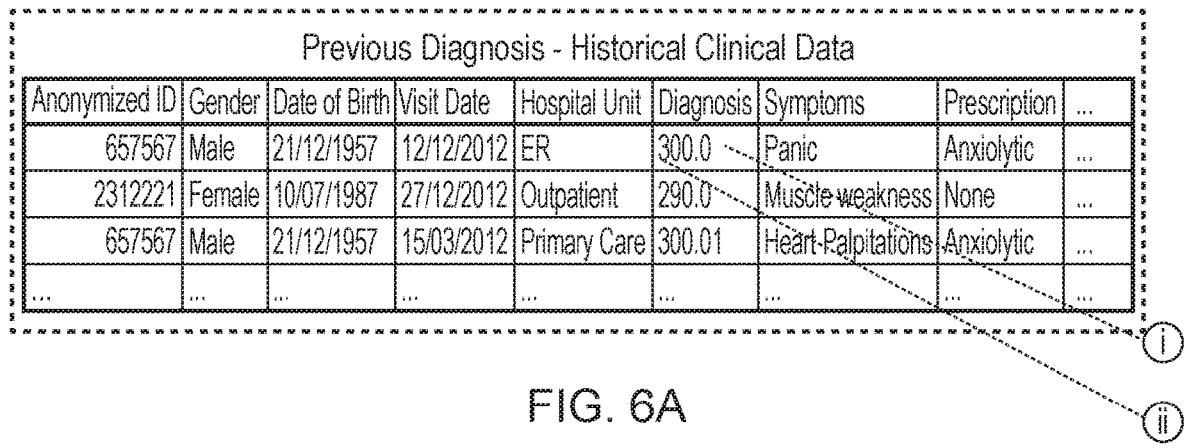
FIGS. 6A, 6B, and 6C are diagrams showing how a PCO can be built.
Figure 6B:
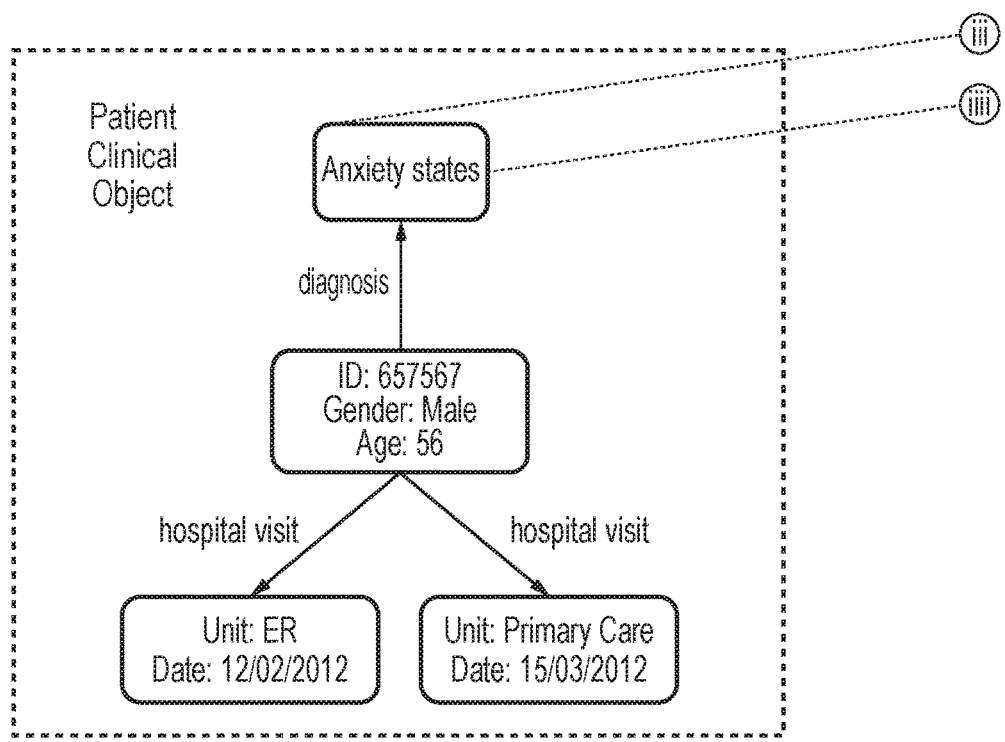
Figure 6C:
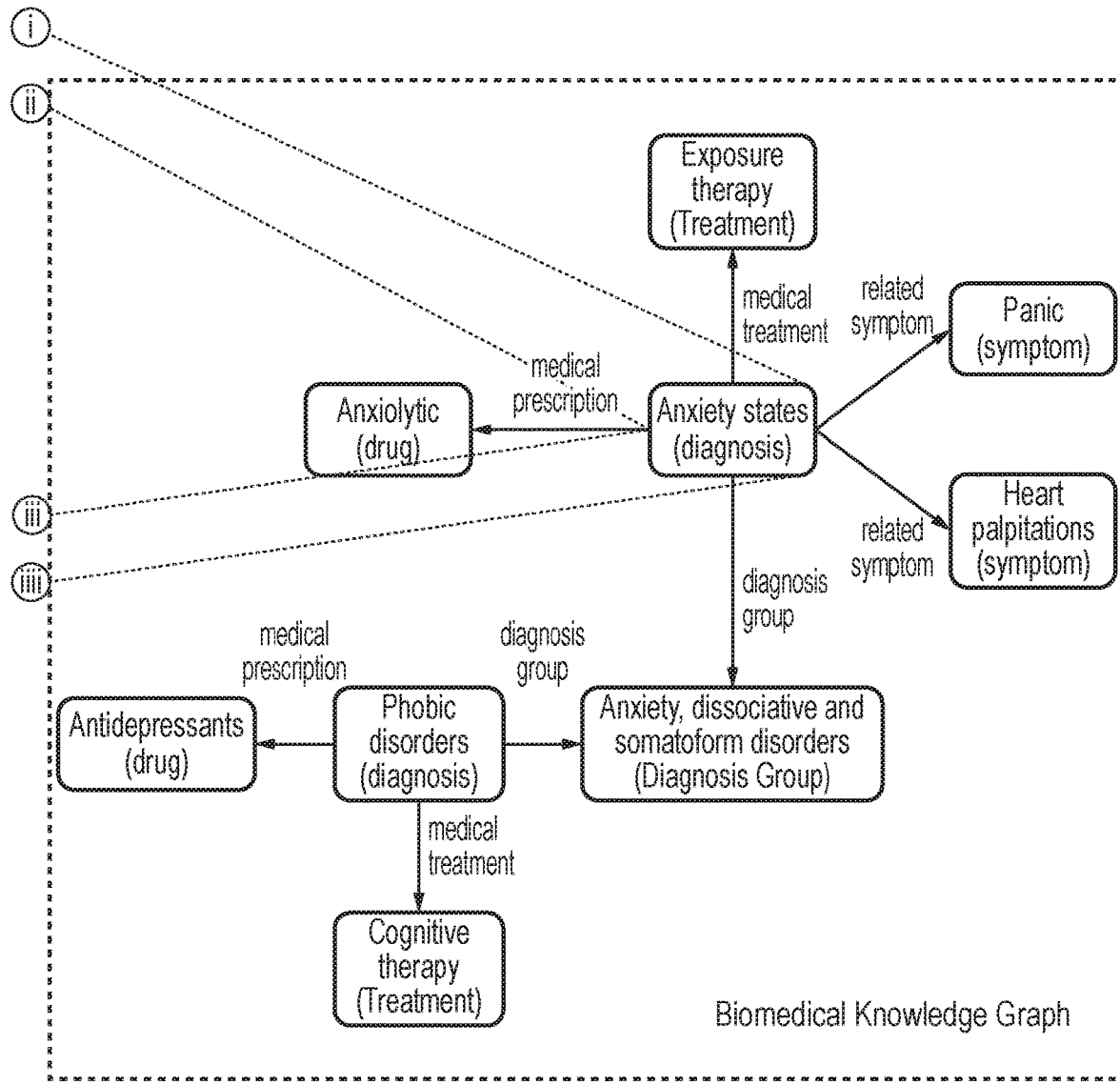

As shown in FIGS. 6A, 6B and 6C, the Patient Clinical Object Builder/Engine takes as input the patient data (previous diagnoses, historical clinical data), and performs data curation, cleaning and pre-processing over such data.

Next, the Patient Clinical Object Enricher identifies all the entities of the patient data, and annotates each one with the concepts/information coming from the Biomedical Knowledge Graph. The outcome of this process is an Enriched Patient Clinical Object which is ready for use.

Figure 7A:
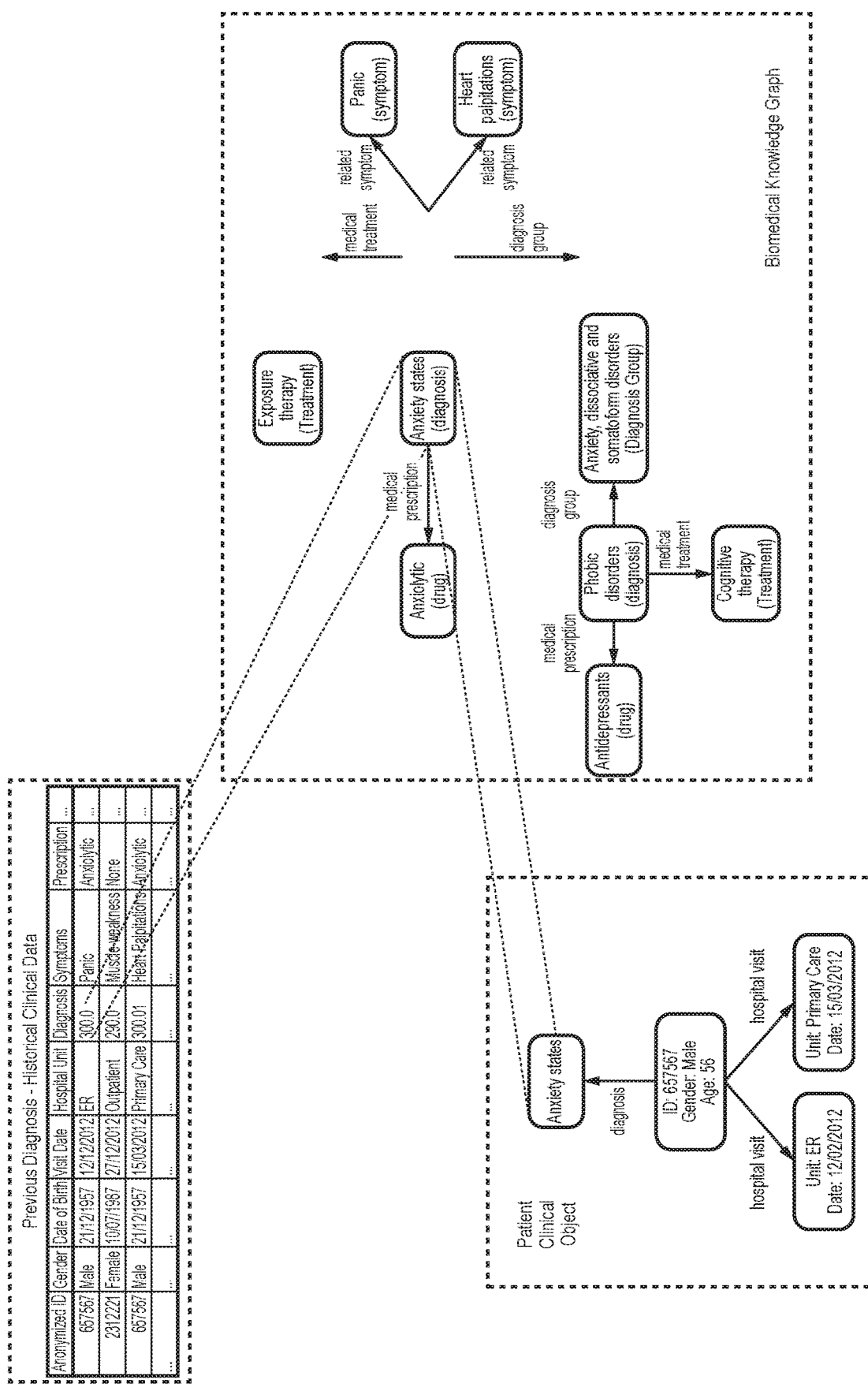
FIG. 7A and FIG. 7B are diagrams showing enrichment of a PCO using the biomedical knowledge graph.
Figure 7B:
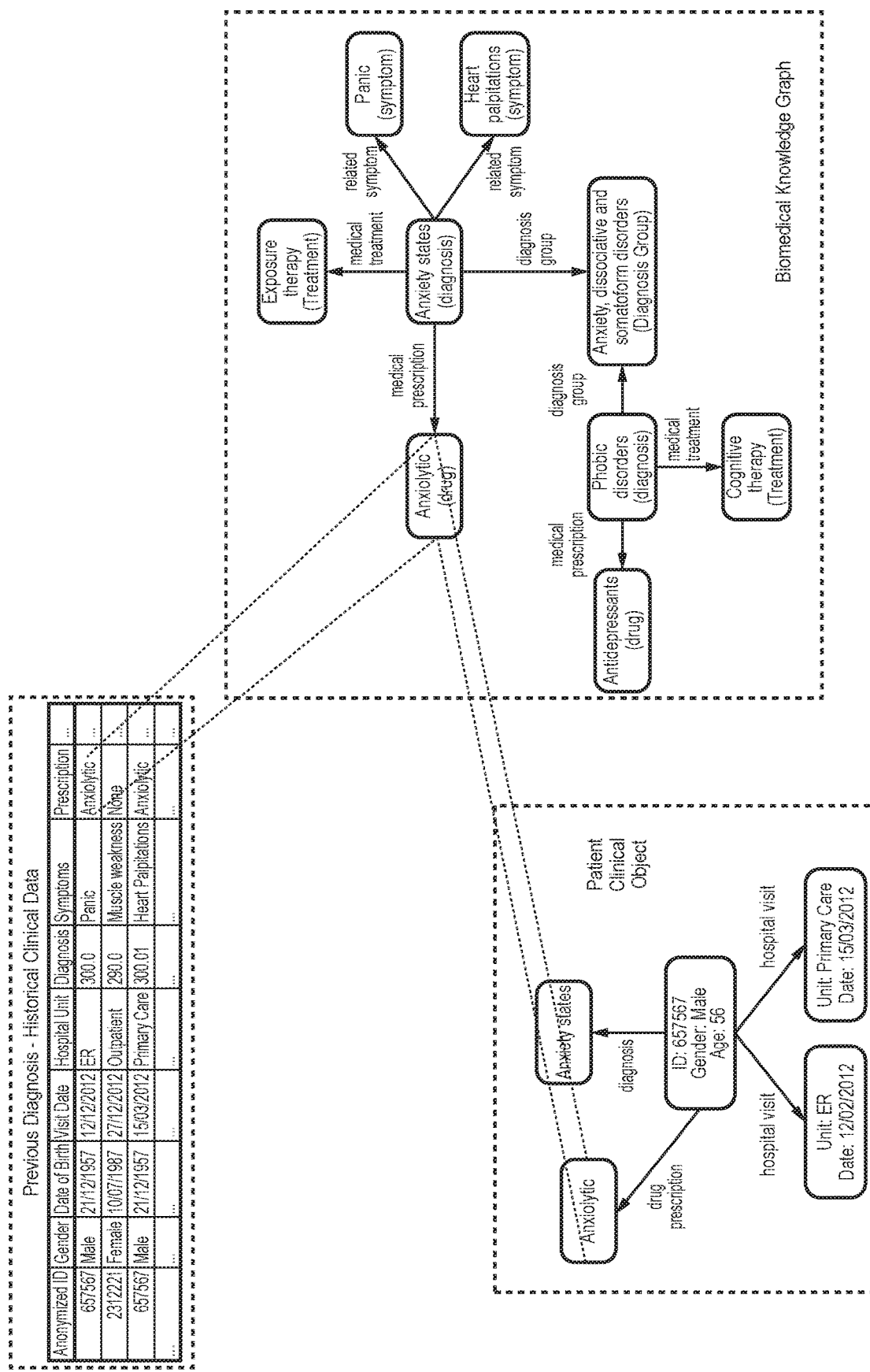

FIGS. 7A and 7B explain the relevant process flow. First, we identify the patient basic information, e.g., gender, age, and visits. Next, by relying on the Biomedical Knowledge Graph we identify that a particular code corresponds to a diagnosis, a string of letters corresponds to a drug, a word corresponds to a symptom and so on.

The PCO (including this additional information) is used in the prediction module.

A detailed example of meta-prediction follows, using the equation as set out previously.

Basically, each predictor outputs a set of diagnoses each ranked based on a score.

The weight for each predictor represents how accurate its diagnoses are. Each weight then represents the number of diagnoses we consider for each predictor. The meta predictor outputs the intersection of the repeated diagnosis of the individual predictors.

For example the predictor based on previous diagnoses may have the following output:

| D | Score |
|---|---|
| 300.00 | 0.7 |
| 290.0 | 0.5 |
| 300.01 | 0.5 |
| 290.01 | 0.4 |

And a weight of 2 represents that we only consider the first two diagnoses (*) for that predictor:

| D | Score |
|---|---|
| *300.00 | *0.7 |
| *290.0 | *0.5 |
| 300.01 | 0.5 |
| 290.01 | 0.4 |

Let us suppose we have the following example $$D_j = W_d P_d + W_{dr} P_{dr} + W_s P_s + W_t P_t$$

And replacing the results of the predictors:

|    | D       | Score  |
|----|---------|--------|
|    | *300.0  | *0.7   |
|    | *290.0  | *0.5   |
|    | 300.01  | 0.5    |
| 2  | 290.01  | 0.4    |
|    | *290.1  | *0.8   |
|    | *290.0  | *0.8   |
|    | *300.01 | *0.7   |
|    | 291.01  | 0.7    |
| +3 | 292.0   | 0.6    |
|    | *290.0  | *0.7   |
|    | *293.0  | *0.6   |
|    | *301.01 | *0.6   |
|    | *296.01 | *0.5   |
|    | 297.0   | 0.4    |
| +4 | 293.1   | 0.4    |
|    | *291.0  | *0.7   |
|    | *290.0  | *0.6   |
|    | 301.01  | 0.5    |
|    | 296.01  | 0.4    |
|    | 297.0   | 0.4    |
| +2 | 293.1   | 0.4    |

Next, the meta predictor checks which diagnoses are present in all the individual predictors and selects the one which has a high score in terms of the largest cumulative score and/or largest number of times it appears. According to our example, the Primary diagnosis is 290.0.

The meta predictor, in order to calculate the weights, is trained in advance on a pre-defined set of training examples, which then facilitate its ability to reach an accurate diagnosis when giving new patient data.

Figure 8:
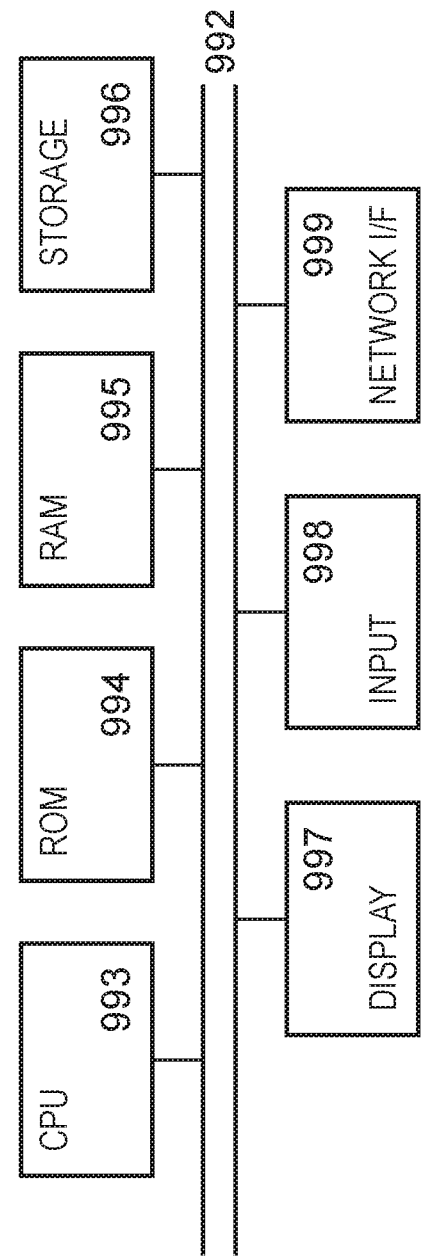
FIG. 8 is a diagram of suitable hardware for implementation of invention embodiments.

FIG. 8 is a block diagram of a computing device, such as a data storage server, which embodies the present invention, and which may be used to implement a method of an embodiment aiding diagnosis. The computing device comprises a computer processing unit (CPU) 993, memory, such as Random Access Memory (RAM) 995, and storage, such as a hard disk, 996. Optionally, the computing device also includes a network interface 999 for communication with other such computing devices of embodiments.

For example, an embodiment may be composed of a network of such computing devices. Optionally, the computing device also includes Read Only Memory 994, one or more input mechanisms such as keyboard and mouse 998, and a display unit such as one or more monitors 997. The components are connectable to one another via a bus 992.

The CPU 993 is configured to control the computing device and execute processing operations. The RAM 995 stores data being read and written by the CPU 993. The storage unit 996 may be, for example, a non-volatile storage unit, and is configured to store data.

The display unit 997 displays a representation of data stored by the computing device and displays a cursor and dialog boxes and screens enabling interaction between a user and the programs and data stored on the computing device. The input mechanisms 998 enable a user (such as a clinician or a group of clinicians or system experts) to input data and instructions to the computing device.

The network interface (network I/F) 999 is connected to a network, such as the Internet, and is connectable to other such computing devices via the network. The network I/F 999 controls data input/output from/to other apparatus via the network. Other peripheral devices such as microphone, speakers, printer, power supply unit, fan, case, scanner, trackerball etc may be included in the computing device.

Methods embodying the present invention may be carried out on a computing device such as that illustrated in FIG. 8. Such a computing device need not have every component illustrated in FIG. 8, and may be composed of a subset of those components. A method embodying the present invention may be carried out by a single computing device in communication with one or more data storage servers via a network. The computing device may be a data storage itself storing at least a portion of the data graph.

A method embodying the present invention may be carried out by a plurality of computing devices operating in cooperation with one another. One or more of the plurality of computing devices may be a data storage server storing at least a portion of a data graph or database.

Although a few embodiments have been shown and described, it would be appreciated by those skilled in the art that changes may be made in these embodiments without departing from the principles and spirit of the invention, the scope of which is defined in the claims and their equivalents.

The invention claimed is:

1. A system to aid diagnosis of a patient, comprising:
an input mechanism and a network interface, and at least one processor coupled to at least one memory, wherein the at least one processor and the at least one memory implement:
a data and knowledge acquisition module and a meta diagnosis prediction module,
wherein,
the data and knowledge acquisition module,
provides an input function for patient data via the network interface including data of previous diagnosis, drugs, symptoms and treatment, an input function for open data via the network interface and an input function for expert knowledge in text file form via the input mechanism,
uses the input patient data, open data and expert knowledge data to store in the at least one memory structured and linked information in form of a plurality of graph databases, each graph database of the graph databases to represent the linked information in form of a patient clinical object (PCO) graph, a biomedical knowledge graph and a rule based knowledge graph, respectively, and
enriches the PCO using the graph database of the biomedical knowledge graph by,
identifying, using the graph database of the biomedical knowledge graph, entities in the input patient data including identifying codes, strings of letters and/or words that correspond to diagnoses, drugs, treatments, and symptoms, and
annotating each entity in the graph database of the PCO with concepts and/or information from the graph database of the biomedical knowledge graph by comparing the graph database of the PCO with the graph database of the biomedical knowledge graph to equate PCO parts including the identified diagnoses, drugs, treatments, and symptoms, of the PCO with a standard vocabulary in the graph database the biomedical knowledge graph to annotate each entity in the graph database of the PCO with corresponding concepts and/or information from the graph database of the biomedical knowledge graph,
wherein,
the data and knowledge acquisition module extracts data from open sources via the network interface to form the graph database of the biomedical knowledge graph that contains information about the diagnoses, drugs, treatments, and symptoms and the links between them, the input function for expert knowledge via the input mechanism allows input of pairs of two diagnoses and a relation between the diagnoses of each pair of two diagnoses that is known to an expert, the data and knowledge acquisition module implements an expert knowledge base inference engine to build the graph database of the rule based knowledge graph from the diagnoses and the relations between the diagnosis, and the data and knowledge acquisition module implements a PCO inference engine to provide the enriched PCO from patient data in form of the graph database of the PCO as a graph centered on the patient with information about the patient linked to the patient by categories including one or more of diagnosis, symptom, treatment, hospital visit or prescription; and wherein, the meta diagnosis prediction module automatically inputs a combination of the graph databases of the enriched PCO and at least the biomedical knowledge graph and/or the rule based knowledge graph into at least two separate computer implemented predictors among plural separate computer implemented predictors including:

a diagnosis-based predictor to provide a set of diagnoses based on previous diagnoses using, from the enriched PCO, entities categorized as previous diagnoses, and using the graph database of the rule-based knowledge graph to add expert knowledge, a drug-based predictor to provide a set of diagnoses based on, from the enriched PCO, entities categorized as drugs taken by the patient, and using the graph database of the biomedical knowledge graph, a symptom-based predictor to provide a set of diagnoses based on, from the enriched PCO, entities categorized as symptoms of the patient, and using the graph database of the biomedical knowledge graph, and a treatment-based predictor to provide a set of diagnoses based on, from the enriched PCO, entities categorized as treatments the patient is receiving, and using the graph database of the biomedical knowledge graph;

wherein, the meta diagnosis prediction module implements a computer implemented meta predictor to combine at least two sets of diagnoses of the at least two separate computer implemented predictors input to the meta predictor to provide an improved predicted primary diagnosis based on the combined at least two sets of diagnoses, the computer implemented meta predictor trained on a set of training examples by the meta diagnosis prediction module prior to the computer implemented meta predictor combining the at least two sets of diagnoses; and the meta diagnosis prediction module, ranks each diagnosis in each set of diagnosis of the at least two sets of diagnoses based on a score, obtains a weighting given to each separate computer implemented predictor based on an accuracy of performance measure derived from the computer implemented meta predictor training on the set of training examples, to determine a number of diagnoses starting from a top-ranking diagnosis, among the ranked diagnosis, in each set of diagnoses of the at least two sets of diagnoses, and outputs the improved predicted primary diagnosis based on the top-ranking diagnosis in each set of diagnoses of the at least two sets of diagnoses by the trained computer implemented meta predictor.

2. A system according to claim 1, wherein the meta diagnosis prediction module makes predictions by organizing and processing separate predictions produced by the separate predictors.

3. A system according to claim 1, wherein the meta predictor checks the diagnoses taken into consideration from the separate predictors and selects one or more which is present in highest number of predictors and/or has highest cumulative score as the improved predicted primary diagnosis.

4. A method by a computer system to aid diagnosis of a patient, comprising:

by at least one processor of the computer system coupled to at least one memory of the computer system, causing the computer system to, accept input of, patient data including data of previous diagnosis, drugs, symptoms and treatment, open data, and expert knowledge;

use the input patient data, open data and expert knowledge data to store in the at least one memory structured and linked information in form of a plurality of graph databases, each graph database of the graph databases to represent the linked information in form of a patient clinical object (PCO) graph, a biomedical knowledge graph and a rule based knowledge graph, respectively; and enrich the PCO using the graph database of the biomedical knowledge graph by, identifying, using the graph database of the biomedical knowledge graph, entities in the input patient data including identifying codes, strings of letters and/or words that correspond to diagnoses, drugs, treatments, and symptoms, and annotating each entity in the graph database of the PCO with concepts and/or information from the graph database of the biomedical knowledge graph by comparing the graph database of the PCO with the graph database of the biomedical knowledge graph to equate PCO parts including the identified diagnoses, drugs, treatments, and symptoms, of the PCO with a standard vocabulary in the graph database the biomedical knowledge graph to annotate each entity in the graph database of the PCO with corresponding concepts and/or information from the graph database of the biomedical knowledge graph;

extract data from open sources to form the graph database of the biomedical knowledge graph that contains information about the diagnoses, drugs, treatments, and symptoms and the links between them, the input of expert knowledge includes input of pairs of two diagnoses and a relation between the diagnoses of each pair of two diagnoses that is known to the expert;

build the graph database of the rule based knowledge graph from the diagnoses and the relations between the diagnoses;
provide the enriched PCO from patient data in form of the graph database of the PCO as a graph centered on the patient with information about the patient linked to the patient by categories including one or more of diagnosis, symptom, treatment, hospital visit or prescription;
automatically input a combination of the graph databases of the enriched PCO and at least the biomedical knowledge graph and/or the rule based knowledge graph into at least two separate computer implemented predictors to obtain predictions of:
a diagnosis-based predicted set of diagnoses based on previous diagnoses using, from the enriched PCO, entities categorized as previous diagnoses, and using the graph database of the rule-based knowledge graph to add expert knowledge,
a drug-based predicted set of diagnoses based on, from the enriched PCO, entities categorized as drugs taken by the patient, and using the graph database of the biomedical knowledge graph,
a symptom-based predicted set of diagnoses based on, from the enriched PCO, entities categorized as symptoms of the patient, and using the graph database of the biomedical knowledge graph, and
a treatment-based predicted set of diagnoses based on, from the enriched PCO, entities categorized as treatments the patient is receiving, and using the graph database of the biomedical knowledge graph;
input to a computer implemented meta predictor at least two sets of diagnoses of the at least two separate computer implemented predictors to combine the at least two sets of diagnosis to provide an improved predicted primary diagnosis based on the combined at least two sets of diagnoses, the computer implemented meta predictor trained on a set of training examples prior to the computer implemented meta predictor combining the at least two sets of diagnoses,
rank each diagnosis in each set of diagnoses of the at least two sets of diagnoses based on a score;
obtain a weighting given to each separate computer implemented predictor based on an accuracy of performance measure derived from the computer implemented meta predictor training on the set of training examples, to determine a number of diagnoses starting from a top-ranking diagnosis, among the ranked diagnosis, in each set of diagnoses of the at least two sets of diagnoses; and
output the improved predicted primary diagnosis based on the top-ranking diagnosis in each set of diagnoses of the at least two sets of diagnoses by the trained computer implemented meta predictor.

5. A non-transitory computer-readable storage medium storing a computer program which when executed on a computer carries out a method to aid diagnosis of a patient, comprising:
accepting input of, patient data including data of previous diagnosis, drugs, symptoms and treatment, open data, and expert knowledge;
using the input patient data, open data and expert knowledge data to store in the at least one memory structured and linked information in form of a plurality of graph databases, each graph database of the graph databases to represent the linked information in form of a patient clinical object (PCO) graph, a biomedical knowledge graph and a rule based knowledge graph, respectively; and
enrich the PCO using the graph database of the biomedical knowledge graph by,
identifying, using the graph database of the biomedical knowledge graph, entities in the input patient data including identifying codes, strings of letters and/or words that correspond to diagnoses, drugs, treatments, and symptoms, and
annotating each entity in the graph database of the PCO with concepts and/or information from the graph database of the biomedical knowledge graph by comparing the graph database of the PCO with the graph database of the biomedical knowledge graph to equate PCO parts including the identified diagnoses, drugs, treatments, and symptoms, of the PCO with a standard vocabulary in the graph database the biomedical knowledge graph to annotate each entity in the graph database of the PCO with corresponding concepts and/or information from the graph database of the biomedical knowledge graph;
extracting data from open sources to form the graph database of the biomedical knowledge graph that contains information about the diagnoses, drugs, treatments, and symptoms and the links between them,
the input of expert knowledge includes input of pairs of two diagnoses and a relation between the diagnoses of each pair of two diagnoses that is known to the expert;
building the graph database of the rule based knowledge graph from the diagnoses and the relations between the diagnoses;
providing the enriched PCO from patient data in form of the graph database of the PCO as a graph centered on the patient with information about the patient linked to the patient by categories including one or more of diagnosis, symptom, treatment, hospital visit or prescription;
automatically inputting a combination of the graph databases of the enriched PCO and at least the biomedical knowledge graph and/or the rule based knowledge graph into at least two separate computer implemented predictors to obtain predictions of:
a diagnosis-based predicted set of diagnoses based on previous diagnoses using, from the enriched PCO, entities categorized as previous diagnoses, and using the graph database of the rule-based knowledge graph to add expert knowledge,
a drug-based predicted set of diagnoses based on, from the enriched PCO, entities categorized as drugs taken by the patient, and using the graph database of the biomedical knowledge graph,
a symptom-based predicted set of diagnoses based on, from the enriched PCO, entities categorized as symptoms of the patient, and using the graph database of the biomedical knowledge graph, and
a treatment-based predicted set of diagnoses based on, from the enriched PCO, entities categorized as treatments the patient is receiving, and using the graph database of the biomedical knowledge graph;
inputting to a computer implemented meta predictor at least two sets of diagnoses of the at least two separate computer implemented predictors to combine the at least two sets of diagnosis to provide an improved predicted primary diagnosis based on the combined at least two sets of diagnoses, the computer implemented meta predictor trained on a set of training examples prior to the computer implemented meta predictor combining the at least two sets of diagnoses, ranking each diagnosis in each set of diagnoses of the at least two sets of diagnoses based on a score;

obtaining a weighting given to each separate computer implemented predictor based on an accuracy of performance measure derived from the computer implemented meta predictor training on the set of training examples, to determine a number of diagnoses starting from a top-ranking diagnosis, among the ranked diagnosis, in each set of diagnoses of the at least two sets of diagnoses;

outputting the improved predicted primary diagnosis based on the top-ranking diagnosis in each set of diagnoses of the at least two sets of diagnoses by the trained computer implemented meta predictor.

* * * * *